US00PP35845P2

(12) United States Plant Patent
McNamara et al.

(10) Patent No.: US PP35,845 P2
(45) Date of Patent: May 28, 2024

(54) ***CEANOTHUS* PLANT NAMED 'UMNCNS01'**

(50) Latin Name: *Ceanothus americanus*
Varietal Denomination: UMNCNS01

(71) Applicant: Regents of the University of Minnesota, Minneapolis, MN (US)

(72) Inventors: Steven Thomas McNamara, Victoria, MN (US); Peter Christian Moe, Excelsior, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 18/235,433

(22) Filed: Aug. 18, 2023

Related U.S. Application Data

(60) Provisional application No. 63/399,732, filed on Aug. 22, 2022.

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Penny J Aguirre

(57) ABSTRACT

A new cultivar of *Ceanothus* plant named 'UMNCNS01' that is characterized by its inflorescences that are light pink in color, its coral red fruit capsules, and its crown cold hardiness to U.S.D.A Zone 4a.

2 Drawing Sheets

STATEMENT REGARDING FEDERALLY SPONSORED RESEARCH

This invention was made with government support under NA/MIN021058 and NA/MIN021055 awarded by the National Institute of Food and Agriculture. The government has certain rights in the invention.

Botanical classification: *Ceanothus americanus*.
Variety denomination: 'UMNCNS01'.

BACKGROUND OF THE INVENTION

The present invention relates to a new and distinct cultivar of *Ceanothus* of hybrid origin, and will be referred to hereafter by its cultivar name, 'UMNCNS01'. 'UMNCNS01' is a new cultivar of deciduous shrub for use as a landscape plant.

'UMNCNS01' resulted from an ongoing research program in Excelsior, Minnesota with the goal of breeding new cultivars of *Ceanothus* that are cold hardy with compact plant habits, and floriferous blooming habits. 'UMNCNS01' originated from open pollination of an unnamed and unpatented proprietary plant of *Ceanothus americanus* from the Inventor's breeding program. The male parent is unknown; however, the seed parent was surrounded by other unnamed and unpatented proprietary plants of *Ceanothus americanus* from the Inventors' breeding program. 'UMNCNS01' was selected as a single unique plant from the resulting seedlings in July of 2008.

Asexual propagation of the new cultivar was first accomplished using softwood stem cuttings by one of the Inventors in Excelsior, MN in July of 2008. Asexual propagation of the new cultivar by softwood stem cuttings has been determined that the characteristics of the clonal propagules are stable and are reproduced true to type.

SUMMARY OF THE INVENTION

The following traits have been repeatedly observed and represent the characteristics 'UMNCNS01'. These attributes in combination distinguish 'UMNCNS01' as a new and distinct cultivar of *Ceanothus*.

1. 'UMNCNS01' exhibits inflorescences that are light pink in color.
2. 'UMNCNS01' exhibits coral red fruit capsules.
3. 'UMNCNS01' exhibits crown cold hardiness to U.S.D.A Zone 4a.

The female parent of 'UMNCNS01' differs from 'UMNCNS01' in having white inflorescences and gray-black fruit capsules. 'UMNCNS01' can be most closely compared to the *Ceanothus* 'Minmarose' (not patented). 'Minmarose' is similar to 'UMNCNS01' in having pink flowers. 'Minmarose' differs from 'UMNCNS01' in having black fruit capsules and in being only hardy in U.S.D.A. Zones 6 to 9.

BRIEF DESCRIPTION OF THE DRAWINGS

The accompanying color photographs illustrate the overall appearance and distinct characteristics of the new *Ceanothus*. The plants in the photograph are 3 years in age as grown outdoors in a trial garden in Excelsior, Minnesota.

The photograph FIG. 1 provides a view of 'UMNCNS01' in bloom.

Figure 1:
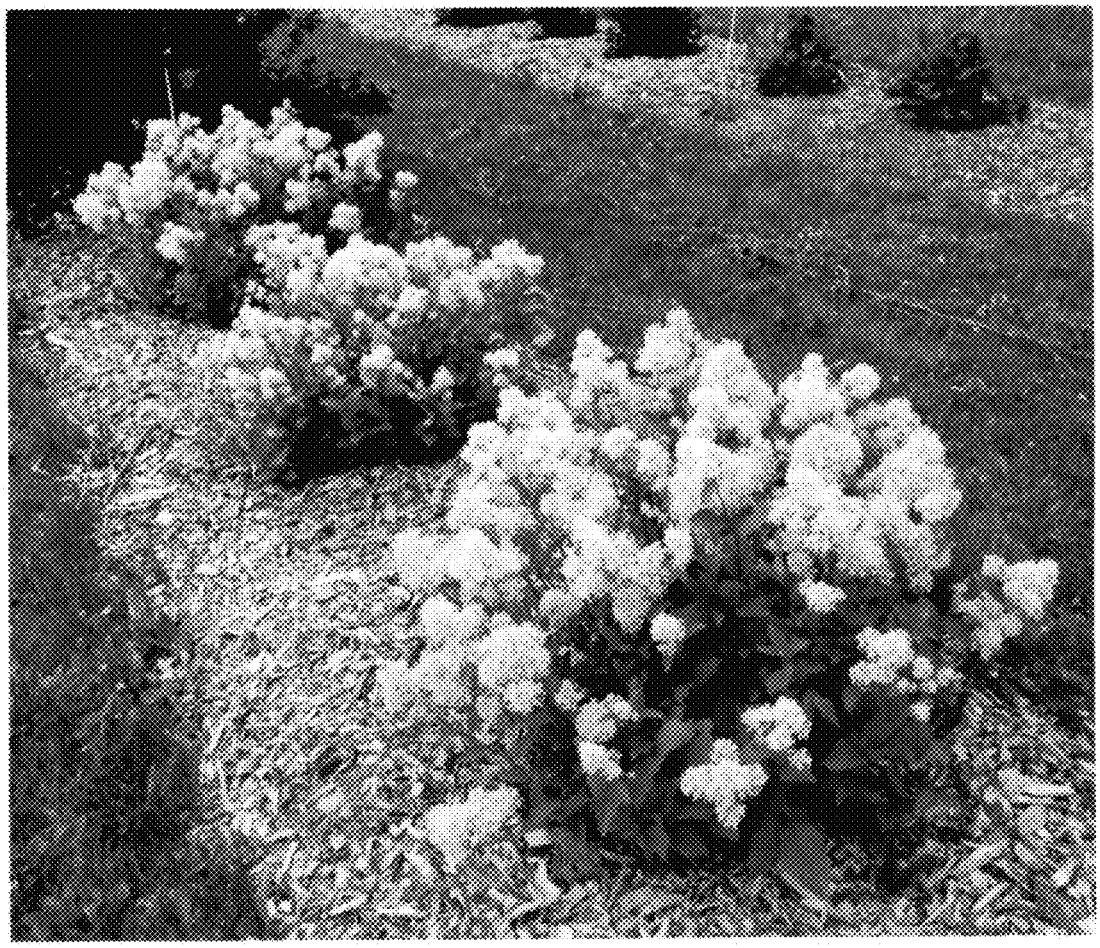
Figure 2:
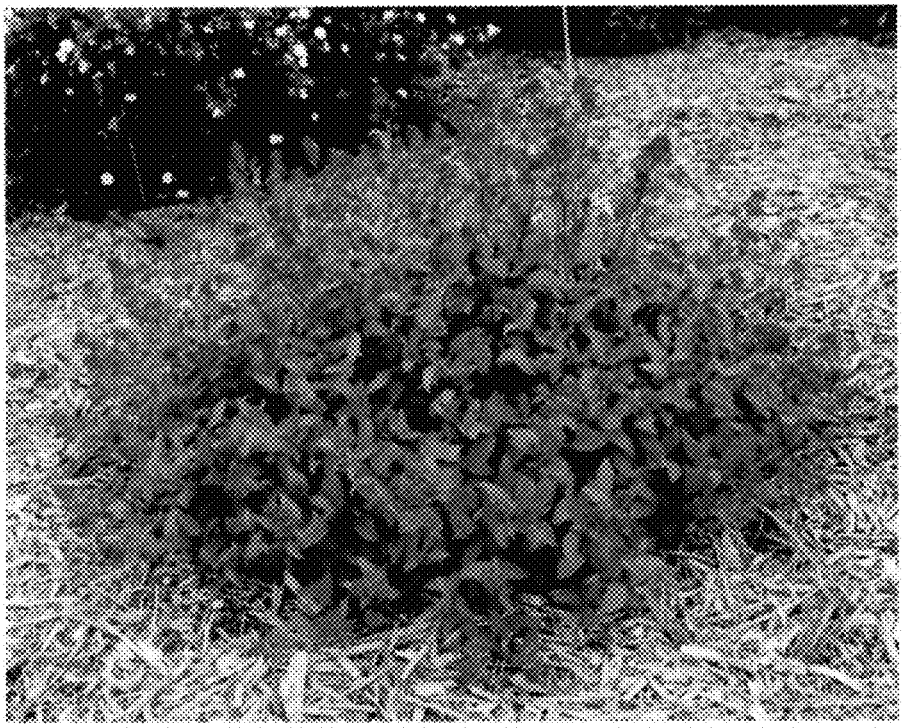

The photograph in FIG. 2 provides a view of 'UMNCNS01' in fruit.

Figure 3:
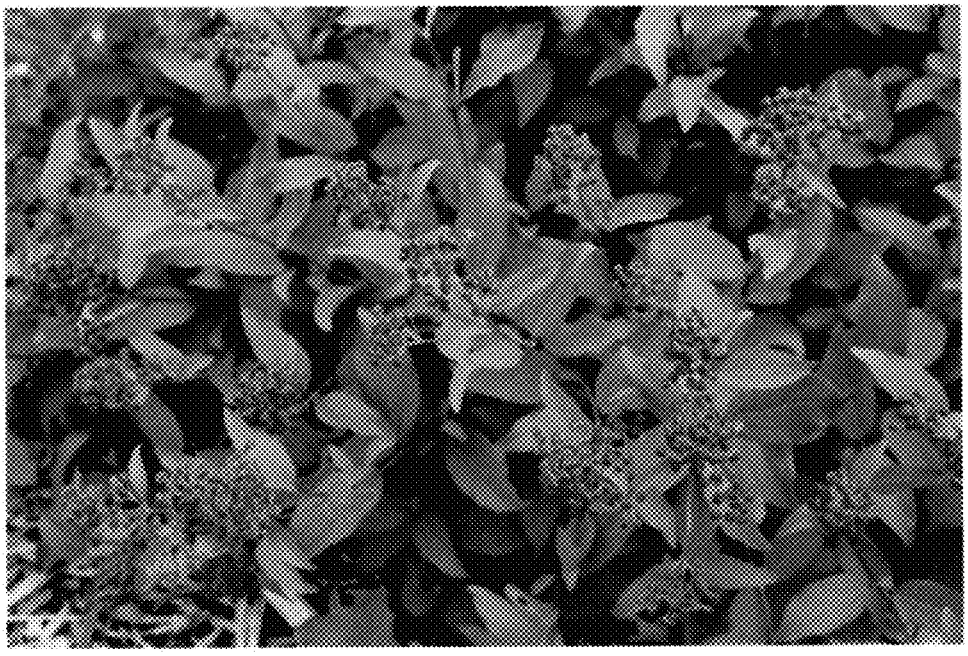

The photograph in FIG. 3 provides a close-up view of the fruit of 'UMNCNS01'.

The colors in the photograph may differ slightly from the color values cited in the detailed botanical description, which accurately describe the colors of the new *Ceanothus*

DETAILED BOTANICAL DESCRIPTION

The following is a detailed description of 4-year-old plants of the new *Ceanothus* as grown in a field plot in Excelsior, Minnesota. The phenotype of the new cultivar may vary with variations in environmental, climatic, and cultural conditions, as it has not been tested under all possible environmental conditions. The color determination is in accordance with The 2007 Colour Chart of The Royal Horticultural Society, London, England, except where general color terms of ordinary dictionary significance are used.

General plant characteristics:

*Blooming period*.—Two weeks in mid to late June in Minnesota.

*Plant type*.—Deciduous shrub.

*Plant habit*.—Compact, spreading mound.

*Blooming period*.—Typically blooms for two weeks in mid- to late-June.

*Height and spread*.—Average of 61.5 cm in height and 1.24 m in width (regrowth in a single season).

*Cold hardiness*.—Crown hardy at least to U.S.D.A. Zone 4a.

*Diseases and pests*.—No susceptibility to resistance to diseases or pests has been observed but appears to be relatively resistant to Japanese beetles (*Popillia japonica*) in trials.

*Root description*.—Fibrous.

*Propagation*.—Softwood stem cuttings.

*Growth rate*.—Moderate.

Stem description:

*Shape*.—Rounded, occasionally flattened.

*Stem color*.—New twigs; 184A on exposed upper surface, 145B on lower surface, mature stems; a blend of 199A and 146C.

*Stem strength*.—Moderately strong.

*Stem size*.—Main stems; an average of 58 cm in length, 3 mm in diameter, lateral stems; 10 to 30 cm in length, 2.5 mm in diameter.

*Branching*.—Average of 75 primary upright sems emerging from crown, lateral stems held in an average angle of 25° to main stems.

*Internode length*.—Average 7.0 cm.

Foliage description:

*Leaf shape*.—Elliptic to ovate.

*Leaf division*.—Simple.

*Leaf base*.—Attenuate.

*Leaf apex*.—Narrowly acute.

*Leaf fragrance*.—None.

*Leaf venation*.—Typically three prominent parallel veins extending from the leaf base to the outer margins of leaf tip, 145C in color.

*Leaf margins*.—Crenate to serrulate.

*Leaf arrangement*.—Alternate.

*Leaf attachment*.—Petiolate.

*Leaf number*.—Average of 11 per main stem, average of 9 per lateral branch.

*Leaf surface*.—Upper surface glabrous, lower surface glabrous.

*Leaf size*.—Average of 6.6 cm in length and 2.9 cm in width.

*Leaf color*.—Young upper surface; 144A young lower surface; 146B, mature upper surface; 147A, mature lower surface; 146B in color, fall color both surfaces; not significant, typically 162D in color.

*Stipules*.—None observed.

Inflorescence description:

*Inflorescence type*.—Compound axillary and terminal panicles consisting of simple umbels.

*Inflorescence number*.—Average of 140.

*Inflorescence size*.—Average of 5.1 cm in height and 2.4 cm in width.

*Flower quantity*.—About 18 per inflorescence.

*Flowering habit*.—Once a year continuously.

*Flowering season*.—Spring (June in Excelsior, MN).

*Response time to flower*.—Approximately 8 months.

*Pedicels*.—Average of 9 mm in length, 3 mm in diameter, 65C to 73B in color, held at a 45° angle to peduncle, covered with very short hairs, <0.1 mm in length and 155D in color.

*Peduncle*.—Average 3.5 cm in length and 1.5 mm in diameter, pubescent, average angle of terminal inflorescences is 0° (straight on top of lateral branch), average angle of axillary inflorescences is 45°, moderately strong, a blend of 145B and 184A in color, covered with fine hairs, 0.1 mm in length, 155B in color.

*Flower buds*.—Flattened globular in shape, 2 mm in length and 1 mm in diameter, a blend of 97A and 98C in color, buds open in approximately 4 days from described stage.

*Flower fragrance*.—Not noticeably fragrant.

*Persistence of flowers*.—Self-cleaning.

*Lastingness of flowers*.—Flowers last about 2 weeks.

*Flower type*.—Single.

*Flower aspect*.—Towards all directions.

*Flower shape*.—Rotate.

*Flower size*.—About 4 mm in diameter and 2 mm in depth.

*Petals*.—5, about 2 mm in length and 1 mm in width, petals not fused, spathulate in shape, margins entire, apex obtuse, rotate arrangement, both surfaces smooth, color: when opening upper and lower surface; 69D, fully open upper and lower surfaces; a blend of 155B to 69D.

*Sepals*.—5, about 2 mm in length and 1 mm in width, triangular in shape, curved inward towards style, margins entire, apex acute, smooth and dull on upper and lower surface, color of immature and mature upper and lower surfaces; ranging between 155B and 69D.

*Calyx*.—Rotate in shape, about 2 mm in length and 2 mm in diameter.

Reproductive organs:

*Gynoecium*.—1 pistil, about 3.0 mm in length, stigma cleft (3 parted) and 69B in color, style is about 1.2 mm in length and 69B in color, ovary is 146B in color.

*Androecium*.—Typically 5 anthers, basifixed, broadly oval in shape and about 3 mm in length, 11C in color, filaments are about 1.1 mm in length and 65C in color, pollen is moderately produced and 12B in color.

*Fruits and seeds*.—Fruit is a sub-globose to triangular capsule, about 4 mm in diameter, color: young; 151C, mature; 184B, underside 152B, occasionally changing to 200A, seeds; rounded and ovate in shape, 200A in color, 2 mm in diameter.

It is claimed:

1. A new and distinct cultivar of *Ceanothus* plant named 'UMNCNS01', as herein illustrated and described.

* * * * *